United States Patent
Pizzoni et al.

(10) Patent No.: US 9,974,803 B2
(45) Date of Patent: May 22, 2018

(54) COMBINATION OF GLYCOSAMINOGLYCANS AND CYCLODEXTRINS

(71) Applicant: APHARM S.r.l., Arona (NO) (IT)

(72) Inventors: Angelo Pizzoni, Arona (IT); Paolo Pizzoni, Arona (IT)

(73) Assignee: APHARM S.R.L., Arona (IT)

(*) Notice: Subject to any disclaimer, the term of this patent is extended or adjusted under 35 U.S.C. 154(b) by 0 days. days.

(21) Appl. No.: 15/105,595

(22) PCT Filed: Dec. 15, 2014

(86) PCT No.: PCT/IB2014/002774
§ 371 (c)(1),
(2) Date: Jun. 17, 2016

(87) PCT Pub. No.: WO2015/092516
PCT Pub. Date: Jun. 25, 2015

(65) Prior Publication Data
US 2017/0035799 A1    Feb. 9, 2017

(30) Foreign Application Priority Data
Dec. 18, 2013 (IT) .............. MI2013A2116

(51) Int. Cl.
A61K 31/728 (2006.01)
A61K 31/737 (2006.01)
A61K 47/40 (2006.01)
A61K 9/00 (2006.01)
A61K 47/36 (2006.01)
A61K 31/724 (2006.01)

(52) U.S. Cl.
CPC .......... *A61K 31/728* (2013.01); *A61K 9/0019* (2013.01); *A61K 31/724* (2013.01); *A61K 31/737* (2013.01); *A61K 47/36* (2013.01); *A61K 47/40* (2013.01); *A61K 9/0021* (2013.01)

(58) Field of Classification Search
None
See application file for complete search history.

(56) References Cited

U.S. PATENT DOCUMENTS

| | | |
|---|---|---|
| 2008/0003257 A1 | 1/2008 | Marcum et al. |
| 2008/0193425 A1 | 8/2008 | Ellsworth |
| 2010/0098764 A1 | 4/2010 | Stroumpoulis et al. |

FOREIGN PATENT DOCUMENTS

| | | |
|---|---|---|
| CH | 705 713 | 5/2013 |
| CN | 1 451 369 | 10/2003 |
| CN | 101 112 381 | 1/2008 |
| CN | 103 301 118 | 9/2013 |
| EP | 1 967 186 | 9/2008 |
| WO | WO 01/66601 | 9/2001 |
| WO | WO 03/041724 | 5/2003 |
| WO | WO 2010/031876 | 3/2010 |
| WO | WO 2013/144867 | 10/2013 |

OTHER PUBLICATIONS

Fagnola, Contact Lens & Anterior Eye 32 (2009) 108-112.*
Pavicic, J Drugs Dermatol Sep. 2011; 10(9): 990-1000.*
International Search Report for PCT/IB2014/002774 dated Feb. 27, 2015, 6 pages.
Written Opinion of the ISA for PCT/IB2014/002774 dated Feb. 27, 2015, 10 pages.
Azqfan: Bionova skincare with nano technology on at 1 a.m., Internet Citation, pp. 1-8 (Apr. 2008).
Sinha et al., "Cyclodextrins as Sustained-Release Carriers", *Pharmaceutical Technology*, vol. 26, No. 10, pp. 36-46 (Oct. 2002).
International Preliminary Report on Patentability and Written Opinion from PCT dated Jun. 21, 2016 in connection with International Application No. PCT/IB2014/002774, 12 pages.

* cited by examiner

*Primary Examiner* — Layla D Berry
(74) *Attorney, Agent, or Firm* — Nixon & Vanderhye P.C.

(57) ABSTRACT

The invention relates to an injectable combination of two specific glycosaminoglycans, hyaluronic acid and chondroitin sulfate, with cyclodextrins and the use of the combination for the treatment of diseases related to the skeletal systems, particularly in the intra-articular treatment, as well as in the intradermal treatment.

6 Claims, No Drawings

COMBINATION OF GLYCOSAMINOGLYCANS AND CYCLODEXTRINS

This application is the U.S. national phase of International Application No. PCT/IB2014/002774 filed 15 Dec. 2014 which designated the U.S. and claims priority to IT Patent Application MI2013A002116 filed 18 Dec. 2013, the entire contents of each of which are hereby incorporated by reference.

BACKGROUND OF THE INVENTION

Glycosaminoglycans are a polysaccharides family formed by the repetition of an uronic acid, a glucuronic or iduronic acid, 1→4 or β 1→3 linked to a hexosamine, glucosamine or galactosamine residue. The hexosamine and hyaluronic acid residues can be sulfated in various ways. In glycosaminoglycan family, in addition to heparin sulfate and heparan sulfate, hyaluronic acid and chondroitin sulfate are also included. Physiologically, glycosaminoglycans are organized in proteoglycans, formed by a protein nucleus to which glycosaminoglycan is linked by means of a connecting region. These structures have a control role in biochemical reactions by means of the captation and release of proteins and growth factors (J. F. Kennedy, C. A. White, Bioactive Carbohydrates, 1983, Ellis Horwood Ltd, 211-227).

In particular, chondroitin sulfate is localized in cartilages and epithelial portion of the gastric mucosa or in the urothelium. It confers the characteristic of elasticity to cartilages and controls the resistance thereof, whereas in mucosa and epithelium it protects the epithelium itself from the acid attack in the case of gastric epithelium and from potassium in the case of urothelium. In diseases where the amount of chondroitin sulfate is low, such as e.g. in gastritis or interstitial cystitis, the administration of chondroitin sulfate helps in alleviating the inflammation and related damages due to the low chondroitin sulfate content.

Chondroitin sulfate is formed by the disaccharide repetition containing β 1→3 glucuronic acid linked to galactosamine which is sulfated or in position 4 or in position 6. In the same molecule both ChSA and ChSC groups are present. Occasionally, small amounts of disulfated and non-sulfated disaccharides can also be present in the polysaccharide chain.

Hyaluronic acid is a non-sulfated glycosaminoglycan formed by a disaccharide linear sequence of 1-3-glucuronic acid linked to a N-acetylglucosamine.

Hyaluronic acid is ubiquitous in epithelial and connective tissues, e.g., but not only, in skin and cartilages.

The use of combinations of chondroitin sulfate and hyaluronic acid in the regeneration of damaged joint cartilages, e.g. due to osteoarthritis, is known.

Also the intradermal use of hyaluronic acid and/or chondroitin sulfate as a filler of soft tissues and mucosae, e.g. as a "filler" in the aesthetic medical treatments, is known.

The above treatments are effective but present the drawback that they need to be repeated very frequently, since the injected components are quickly reabsorbed by the recipient organism.

OBJECTS OF THE INVENTION

It is an object of the invention to provide a combination of active ingredients useful for the intradermal and intra-articular administration, which brings effective and long-lasting results.

It is a further object of the invention to provide a fixed combination of hyaluronic acid, chondroitin sulfate and a cyclodextrin, for the intradermal and intra-articular administration.

It is a further object of the invention the use of the combination of the invention for the treatment of osteo-skeletal diseases, in particular intra-articular diseases.

It is a further object of the invention the use of the combination of the invention for the aesthetic medical treatment, in particular as "filler" for soft tissues and mucosae.

DESCRIPTION OF THE INVENTION

Therefore, according to one of its aspects, the object of the invention is a pharmaceutical combination consisting of hyaluronic acid, chondroitin sulfate and at least one cyclodextrin.

Unless otherwise specified, in the present description the terms "hyaluronic acid" and "chondroitin sulfate" refer to, each independently, hyaluronic acid and chondroitin sulfate as such, or e.g. in the form of a pharmaceutically acceptable salt thereof, and according to a preferred embodiment, in the form of sodium salts thereof.

Hyaluronic acid and chondroitin sulfate, as defined above, are known in the art and, according to the present invention, can be of any origin, e.g. even of biotechnological and/or fermentative origin.

According to a preferred embodiment, the hyaluronic acid is not of animal origin. Still according to a preferred embodiment the hyaluronic acid has an average molecular weight comprised between 100,000 Da and 5,000,000 Da, advantageously between 500,000 Da and 3,000,000 Da, preferably from about 1,000,000 Da and 2,500,000 Da, e.g., 1,000,000 Da, or even more preferably around 2,000,000 Da.

According to another particularly advantageous embodiment, the hyaluronic acid has an average molecular weight of 3,000,000 Da.

For chondroitin sulfate the average molecular weight is not critical and is generally from 5,000 to 100,000, advantageously from 10,000 Da to 50,000 Da, still more preferably from 10,000 Da to 40,000 Da; other molecular weights can however be used.

The expression "at least one cyclodextrin" defines herein a family of natural cyclic oligosaccharides formed by 6, 7 or 8 glycosidic units linked together and cyclized. Cyclodextrins are commercially available compounds and widely used in the pharmaceutical field.

The term "cyclodextrin", as used herein, refers to any pharmaceutically acceptable cyclodextrin and comprises cyclodextrins derivatives as well, e.g. the polysulfate derivatives, such as those described in EP1301192, or the hydroxy-propylic derivatives which show a better tolerability when used parenterally e.g. by injection.

Usable cyclodextrins according to the present invention are beta-cyclodextrins, e.g. hydroxypropyl-beta-cyclodextrin.

Unless otherwise recommended, in the present description the ratios between the components of the combination are always expressed as weight/weight (w/w) ratios.

Preferably, the combination of the invention is a fixed combination, i.e. a combination in which fixed ratios of the components are used.

According to an embodiment, the ratios one to the other between the components hyaluronic acid and chondroitin sulfate are about 1:1, w/w.

According to a preferred embodiment, in the combination of the invention, the ratios one to the other between the components sodium hyaluronate and sodium chondroitin sulfate are 1:1, w/w.

Still according to a preferred embodiment of the invention, the cyclodextrin component is advantageously present in the fixed combination in a smaller amount; preferably the ratio of the fixed combination will be sodium hyaluronate/sodium chondroitin sulfate/cyclodextrin=1/1/0.3-0.8.

For example, the weight ratio of the components in a representative fixed composition of the invention comprises sodium hyaluronate/sodium chondroitin sulfate/cyclodextrin in a ratio of 1/1/0.5.

Preferably, in the fixed combination of the invention, the weight ratio of the components hyaluronic acid/chondroitin sulfate/hydroxypropyl-beta-cyclodextrin is 1/1/0.5.

All the components of the combination of the invention are commercially available.

The combination of the invention can be used in intradermal and intra-articular, therapeutic and prophylactic treatments.

For example, by means of the intra-articular treatment, the combination can be used as a physical-mechanical agent of viscosupplementation, as a replacement of the synovial fluid in articulations affected by degenerative or mechanical arthropathy which causes pains and reduced mobility, or else as an activator of tissue regeneration processes at the level of articular cartilage.

By means of the intradermal treatment, the combination can be used as a filling agent of soft tissues and mucosae, i.e. as "biorevitalizer" and/or "filler" to fill wrinkles and expression lines, reshape the profile and give volume to lips or other face and body parts.

Such uses and methods of treatment represent a further aspect of the present invention.

For the use according to the invention the combination, in particular the fixed combination, is preferably formulated in pharmaceutically compositions for the intra-articular and intradermal use, in particular in sterile liquid compositions suitable to said administrations. Such compositions represent a further aspect of the invention.

Such compositions are prepared according to techniques known to those skilled in the field, e.g. by dissolving the components of the combinations in a liquid suitable for the intra-articular and intradermal administration, advantageously in a buffered physiological solution, e.g. with sodium chloride, optionally by adding conventional excipients and additives, such as e.g. stabilizers, buffers, etc.

Such compositions will be prepared, for obvious administration requirements, in a sterile way or however sterilized prior to their use. The compositions will be then injected in the human or in the animal (e.g. in mammals such as dogs, horses, etc.).

According to a preferred embodiment, the compositions of the invention contain 0.5 to 4%, advantageously 1 to 4% of hyaluronic acid (w/v, as such or, preferably, in the form of a pharmaceutically acceptable salt thereof, advantageously sodium salt), 0.5 to 4%, advantageously 1 to 4% of chondroitin sulfate (w/v, as such or, preferably, in the form of a pharmaceutically acceptable salt thereof, advantageously sodium salt) and 0.5 to 2% w/v of at least one cyclodextrin, advantageously of hydroxypropyl-beta-cyclodextrin.

According to an embodiment of the invention, the compositions of the invention are liquid and contain about 2% (w/v, e.g. 40 mg in 2 ml of composition) of hyaluronic acid (as such or in the form of a pharmaceutically acceptable salt thereof, preferably sodium salt), about 2% (w/v, e.g. 40 mg in 2 ml of composition) of chondroitin sulfate (as such or in the form of a pharmaceutically acceptable salt thereof, preferably sodium salt) and about 1% (w/v, e.g. 20 mg in 2 ml of composition) of at least one cyclodextrin, preferably hydroxypropyl-beta-cyclodextrin.

According to a particularly advantageous embodiment of the invention, the compositions of the invention are liquid and contain about 2% (w/v, e.g. 60 mg in 3 ml of composition) of hyaluronic acid (as such or in the form of a pharmaceutically acceptable salt thereof, preferably sodium salt), about 2% (w/v, e.g. 60 mg in 3 ml of composition) of chondroitin sulfate (as such or in the form of a pharmaceutically acceptable salt thereof, preferably sodium salt) and about 1% (w/v, e.g. 30 mg in 3 ml of composition) of at least one cyclodextrin, preferably of hydroxypropyl-beta-cyclodextrin.

The amounts of the components of the combination in the composition of the invention are provided as weight/volume of liquid composition, and always refer to the weight of the unsalified components.

According to a preferred embodiment, the compositions of the invention are contained in a ready-to-use syringe, advantageously in a 2 ml syringe containing about 2% (w/v, i.e. 40 mg) of hyaluronic acid (as such or in the form of a pharmaceutically acceptable salt thereof, preferably sodium salt), about 2% (w/v, i.e. 40 mg) of chondroitin sulfate (as such or in the form of a pharmaceutically acceptable salt thereof, preferably sodium salt) and about 1% (w/v, i.e. 20 mg) of at least one cyclodextrin, preferably hydroxypropyl-beta-cyclodextrin.

According to a particularly preferred embodiment, the compositions of the invention are contained in a ready-to-use syringe, advantageously in a 3 ml syringe containing about 2% (w/v, i.e. 60 mg) of sodium hyaluronate, about 2% (w/v, i.e. 60 mg) of sodium chondroitin sulfate and about 1% (w/v, i.e. 30 mg) of at least one cyclodextrin, preferably hydroxypropyl-beta-cyclodextrin.

According to a preferred embodiment, the object of the invention is also a 3 ml pre-filled syringe containing a sterile liquid composition comprising 60 mg of sodium hyaluronate for injectable preparations (average MW 3,000,000 Da), 60 mg of sodium chondroitin sulfate for injectable preparations and 30 of hydroxypropyl-beta-cyclodextrin, together with pharmaceutically acceptable excipients and carriers.

Preferred compositions of the invention will contain, in addition to the combination and the water for injectable preparations, one or more additives as well, e.g. selected from apyrogenic sodium chloride, sodium phosphate dibasic and sodium phosphate monobasic.

When the compositions of the invention are used for intra-articular administration, they can also contain other active ingredients, such as anti-inflammatory agents, e.g. selected from non-steroidal anti-inflammatory drugs and steroidal anti-inflammatory drugs (cortisonics).

Due to the various beneficial properties of methylsulfonylmethane, this component can be added as well to the compositions of the invention intended for intra-articular use.

Representative compositions of the invention are reported in detail in the experimental section of the present description.

The invention also relates to a pharmaceutical composition according to the invention for the use in the treatment or prevention of cartilages degeneration and arthrosis or arthritis diseases or as a filling agent of soft tissues and mucosae.

The invention also relates to a method for the treatment or prevention of cartilages degeneration and arthrosis or arthritis diseases or as a filling agent of soft tissues and mucosae, which comprises administering, to a subject in need of it, an effective amount of a combination or composition as described above.

With respect to known compositions comprising only hyaluronic acid and/or chondroitin sulfate, it has been shown that the combination of the invention provides the advantage of remaining longer in the site where it is injected. In fact, the presence of the cyclodextrin allows to slow down the reabsorption of the other two components of the combination by the treated organism. It is therefore clear that it is requested a less frequent injection of the compositions comprising the combination thus significantly improving the compliance of the treated subject. The following examples are reported exclusively for illustrative purposes and they are absolutely not limitative of the invention.

EXPERIMENTAL SECTION

Example 1

Example of Composition According to the Invention 2 ml of sterile liquid composition contains:
40 mg of sodium hyaluronate for injectable preparations (average MW 2,000,000 Da)
40 mg of sodium chondroitin sulfate for injectable preparations
20 mg of hydroxypropyl-beta-cyclodextrin
17.85 mg of apyrogenic sodium chloride
0.33 mg of anhydrous sodium phosphate dibasic
0.09 mg of sodium phosphate monobasic dihydrate
water for injectable preparation as required to 2 ml Example 2

Example of Composition According to the Invention 2 ml of sterile liquid composition contains:
30 mg of sodium hyaluronate for injectable preparations (average MW 2,000,000 Da)
30 mg of sodium chondroitin sulfate for injectable preparations
15 mg of hydroxypropyl-beta-cyclodextrin
17.85 mg of apyrogenic sodium chloride
0.33 mg of anhydrous sodium phosphate dibasic
0.09 mg of sodium phosphate monobasic dihydrate
water for injectable preparation as required to 2 ml Example 3

Example of Composition According to the Invention 2 ml of sterile liquid composition contains:
30 mg of sodium hyaluronate for injectable preparations (average MW 2,000,000 Da)
30 mg of sodium chondroitin sulfate for injectable preparations
15 mg of hydroxypropyl-beta-cyclodextrin
12.80 mg of apyrogenic sodium chloride
0.25 mg of anhydrous sodium phosphate dibasic
0.06 mg of sodium phosphate monobasic dihydrate
water for injectable preparation as required to 2 ml Example 4

Example of Composition According to the Invention 2 ml of sterile liquid composition contains:
50 mg of sodium hyaluronate for injectable preparations (average MW 2,000,000 Da)
50 mg of sodium chondroitin sulfate for injectable preparations
25 mg of hydroxypropyl-beta-cyclodextrin
17.85 mg of apyrogenic sodium chloride
0.33 mg of anhydrous sodium phosphate dibasic
0.09 mg of sodium phosphate monobasic dihydrate
water for injectable preparation as required to 2 ml Example 5

Example of Composition According to the Invention 2 ml of sterile liquid composition contains:
50 mg of sodium hyaluronate for injectable preparations (average MW 2,000,000 Da)
50 mg of sodium chondroitin sulfate for injectable preparations
25 mg of hydroxypropyl-beta-cyclodextrin
22.30 mg of apyrogenic sodium chloride
0.41 mg of anhydrous sodium phosphate dibasic
0.11 mg of sodium phosphate monobasic dihydrate
water for injectable preparation as required to 2 ml Example 6

A 3 ml syringe contains the following sterile liquid composition:
60 mg of sodium hyaluronate for injectable preparations (average MW 3,000,000 Da)
60 mg of sodium chondroitin sulfate for injectable preparations
30 mg of hydroxypropyl-beta-cyclodextrin
25.50 mg of apyrogenic sodium chloride
0.48 mg of anhydrous sodium phosphate dibasic
0.13 mg of sodium phosphate monobasic dihydrate
water for injectable preparation as required to 3 ml Example 7

Step 1: Method for the Evaluation of the Hyaluronic Acid Degradation

Enzymatic treatment of hyaluronic acid with hyaluronidase at 37° C. for different times. Monitoring of degradation products by means of the Morgan-Elson Assay. The reaction has been blocked by means of tetraborate addition, heated to boiling for 5 minutes. After cooling, by means of DMAB (p-methylaminobenzaldehyde) addition, after 1 hour of incubation, there is a colorimetric development proportional to the amount of spectrophotometrically measurable degraded hyaluronic acid.

The quantification of the hyaluronic acid has been verified before and after the treatment with a second analytical method in order to confirm the obtained results. HPLC-UV analysis on specific Nucleogel (Macherey-nagel GFC 300.8) column.

Step 2: Evaluation of Hyaluronic Acid Stability 3 different mixtures containing hyaluronic acid in a sterile environment have been prepared:
a) Hyaluronic acid alone
b) Hyaluronic acid+chondroitin sulfate
c) Hyaluronic acid+chondroitin sulfate+cyclodextrin polysulfate The stability of the mixtures against enzymatic degradation has been then evaluated at different times.

With respect to formulations (a) and (b), formulation (c) showed a better protection against enzymatic degradation.

The invention claimed is:

1. A pharmaceutical combination comprising hyaluronic acid or a pharmaceutically acceptable salt thereof, chondroitin sulfate or a pharmaceutically acceptable salt thereof, and at least one cyclodextrin;
   wherein the hyaluronic acid has an average molecular weight comprised between 100,000 Da and 5,000,000 Da, and
   wherein the ratio by weight of the three components hyaluronic acid/chondroitin sulfate/cyclodextrin is 1/1/0.5 (w/w).

2. A pharmaceutical combination comprising hyaluronic acid or a pharmaceutically acceptable salt thereof, chondroitin sulfate or a pharmaceutically acceptable salt thereof, and at least one cyclodextrin;
   wherein the hyaluronic acid has an average molecular weight comprised between 100,000 Da and 5,000,000 Da, and
   wherein it consists of a fixed combination of sodium hyaluronate/sodium chondroitin sulfate/hydroxypropyl-cyclodextrin in a 1/1/0.5 ratio (w/w).

3. A pharmaceutical composition in the form of a liquid injectable solution,
   wherein the pharmaceutical combination comprises hyaluronic acid or a pharmaceutically acceptable salt thereof, chondroitin sulfate or a pharmaceutically acceptable salt thereof, and at least one cyclodextrin;
   wherein the hyaluronic acid has an average molecular weight comprised between 100,000 Da and 5,000,000 Da;
   wherein the pharmaceutical composition is in combination with one or more pharmaceutically acceptable excipients;
   wherein it comprises 1 to 4% (w/v) of hyaluronic acid (as such or in the form of a pharmaceutically acceptable salt thereof), 1 to 4% (w/v) of chondroitin sulfate (as such or in the form of a pharmaceutically acceptable salt thereof) and 0.5 to 2% (w/v) of at least one cyclodextrin.

4. The pharmaceutical composition according to claim 3, wherein it comprises 2% (w/v) of sodium hyaluronate, 2% (w/v) of sodium chondroitin sulfate and 1% (w/v) of at least one cyclodextrin.

5. A pharmaceutical composition in the form of a liquid injectable solution,
   wherein the pharmaceutical combination comprises hyaluronic acid or a pharmaceutically acceptable salt thereof, chondroitin sulfate or a pharmaceutically acceptable salt thereof, and at least one cyclodextrin;
   wherein the hyaluronic acid has an average molecular weight comprised between 100,000 Da and 5,000,000 Da;
   wherein the pharmaceutical composition is in combination with one or more pharmaceutically acceptable excipients; and
   wherein said cyclodextrin is hydroxypropyl-beta-cyclodextrin.

6. A pre-filled syringe containing a pharmaceutical composition;
   wherein the pharmaceutical composition in the form of a liquid injectable solution;
   wherein the pharmaceutical combination comprises hyaluronic acid or a pharmaceutically acceptable salt thereof, chondroitin sulfate or a pharmaceutically acceptable salt thereof, and at least one cyclodextrin;
   wherein the hyaluronic acid has an average molecular weight comprised between 100,000 Da and 5,000,000 Da;
   wherein the pharmaceutical composition is in combination with one or more pharmaceutically acceptable excipients; and
   wherein it is a 3 ml syringe and contains a sterile liquid composition comprising 60 mg of sodium hyaluronate for injectable preparations (average MW 3,000,000 Da), 60 mg of sodium chondroitin sulfate for injectable preparations and 30 mg of hydroxypropyl-beta-cyclodextrin, together with pharmaceutically acceptable excipients and carriers.

\* \* \* \* \*